Figure 1:
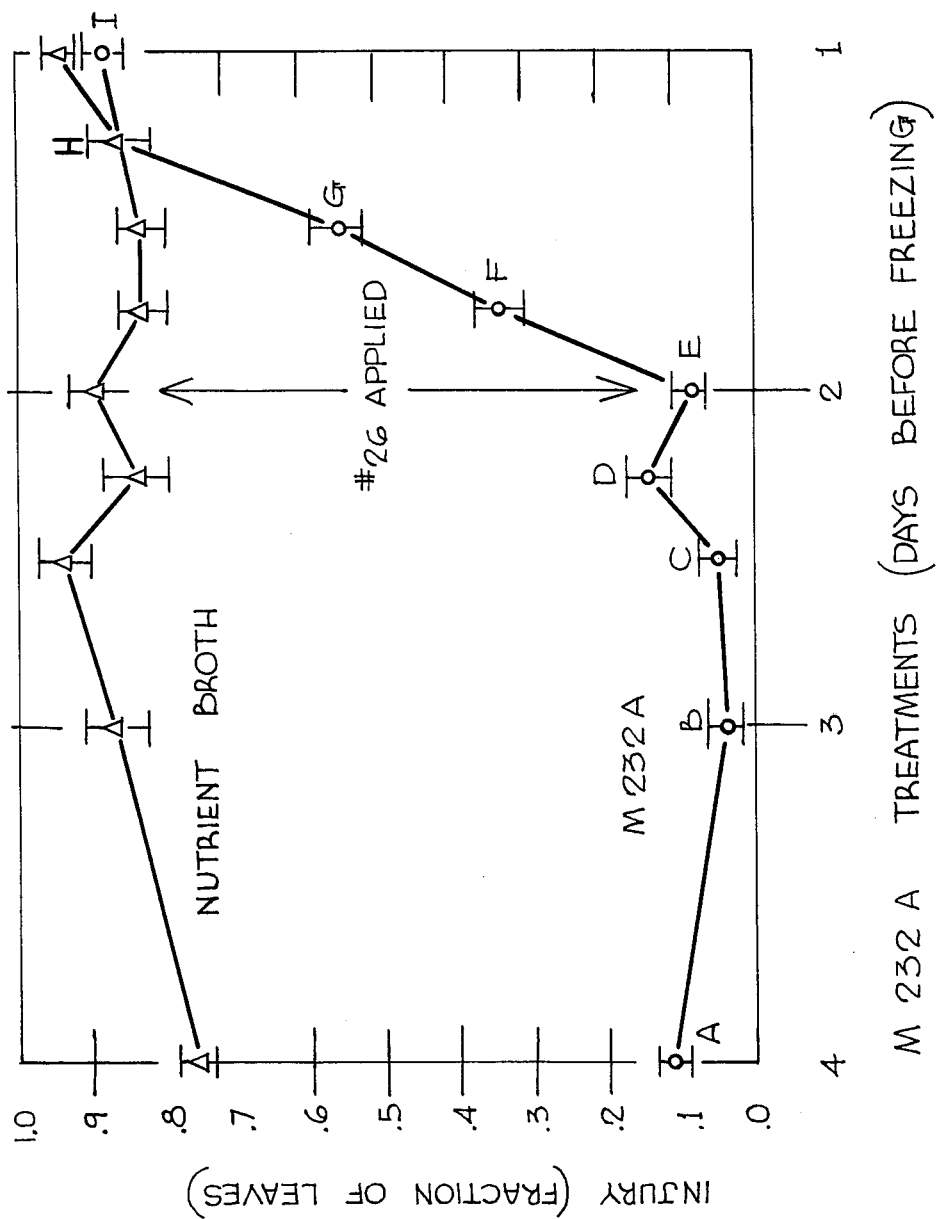

United States Patent [19]

Arny et al.

[11] 4,045,910
[45] Sept. 6, 1977

[54] METHOD FOR REDUCING FROST DAMAGE OF PLANTS

[75] Inventors: Deane C. Arny; Steven E. Lindow, both of Madison, Wis.

[73] Assignee: Wisconsin Alumni Research Foundation, Madison, Wis.

[21] Appl. No.: 710,414

[22] Filed: Aug. 2, 1976

[51] Int. Cl.² .............................................. A01G 1/00

[52] U.S. Cl. .............................................. 47/2; 47/58; 424/93; 195/DIG. 2

[58] Field of Search .......................... 47/2, 58; 424/93; 195/DIG. 2

Primary Examiner—Robert E. Bagwill
Attorney, Agent, or Firm—McDougall, Hersh & Scott

[57] ABSTRACT

The protection of plants against frost damage comprising treating the plants before the onset of freezing cold with bacterium M232A.

4 Claims, 1 Drawing Figure

METHOD FOR REDUCING FROST DAMAGE OF PLANTS

The invention described herein was made in the course of work supported in part under a grant or award from the Department of Health, Education, and Welfare.

This invention relates to frost protecting bacteria and the use thereof in the protection of plants against damage by frost or freezing.

Every year millions of acres of crops and plants are damaged or destroyed by early frost or freezing in temperate or subtropical regions. Such widespread damage has resulted in food shortage and crop failures costing millions of dollars.

Considerable effort has been expended by way of research, development and commercial practice to protect plants and crops against damage by frost or freezing. Use has been made of smudge pots for generating a cover of smoke or smudge to protect the plants by preventing heat loss by radiation, but this is but a temporary protection which is ineffective under windy conditions, while being expensive and of questionable value.

Wind machines are used in some cases to prevent inversions or stratification of cold air.

Use has also been made of water sprays to wet the plants correspondingly to protect the plants against freezing. It requires expensive irrigation equipment and considerable volumes of water. Its effectiveness again is only temporary.

It is an object of this invention to provide a means and method for protection of plants and crops against damage by frost or freezing, wherein such means for protection can be easily applied with readily available equipment, in which it is not essential for the protection means, during application, to reach every part of the plant in order to be effective, in which the protection last for several days so that there is no need to provide the protection means immediately in advance of the onset of frost, thereby to provide greater flexibility in coverage and effectiveness of utilization, which apparently does not interfere with the normal growth of the plant, and which apparently is effective when used with all types of normal plants and crops to prevent frost damage.

It has been established that there are bacteria that naturally occur on plants which act as ice formation nuclei and thus expose the plants to frost or freezing damage at relatively warm temperatures, i.e. $-2°$ to $-4°$ C. Representative of such bacteria are *Pseudomonas syringae*, a plant pathogen, and *Erwinia herbicola*, which is not a plant pathogen. Both of these are commonly found on above ground plant parts. In the absence of these bacteria, freezing occurs at lower temperatures, i.e. about $-6°$ C.

Applicants have found a means to reduce the temperature of ice formation whereby protection can be provided which lasts over a period of time against damage by frost or freezing. The desired protection has been achieved by treatment of the plants with a non-ice nucleation active strain of *Erwinia herbicola* var. ananus, identified as M232A, of which a culture deposit has been made at American Type Culture Collection, 1230 Parklawn Dr., Rockville, Md. 20852 and identified by the number ATCC 31225. The bacterium can be grown under aerobic conditions in normal nutrient media. Abundant growth can be obtained by streaking a small amount of M232A (from a single 2 mm colony) onto a nutrient agar plate containing 20 ml of nutrient broth solidified with 1.5% agar in a petri plate using a sterile platinum loop. (Nutrient broth is made up of 1 gram beef extract, 2 grams yeast extract and 4 grams peptone per liter distilled water.) Large amounts of M232A can be harvested after two days growth at 28° C under normal aerobic conditions. The bacterium retains viability under freeze drying.

Bacterium M232A can be applied to plants in aqueous medium with the application being most readily accomplished by suspending the M232A cells in such medium and spraying the suspension on the plants. If desired, a nutrient, which will aid in proliferation of the bacterium on the plant after spraying, can be added to the suspension. It will be obvious that the concentration of cells in the suspension can vary. For example, it has been found that concentrations of from about $10^6$ to about $10^8$ cells/ml of the suspension are suitable to accomplish the ends of this invention. It is also obvious that the rate of application of the cell suspension will also vary depending upon the type of crop which it is desired to protect from freezing and the method by which it is applied, e.g. aerial or ground rig spraying. For example, protection of corn was afforded by spraying from a ground operated spraying rig a suspension of $10^7 - 10^8$ cells/ml in a nutrient broth one-half the strength of that described above at a rate of 100 gal/acre. In all cases, sufficient of the bacterium must be applied to achieve the freezing protection desired while the adverse economics of applying at too great a rate will obviously dictate the maximum rate of application.

The bacterium is of the rod-like type with flagellae which make it mobile. Thus they may be able to distribute themselves in a relatively short period of time, even through application may be made somewhat unevenly.

The importance of the rate of deposition for the amount of bacterium deposited on the plant is not significant since the bacterium propagates very rapidly, especially when deposited on the plants in nutrient media. In laboratory tests, the bacterium has been applied by liquid spray in which the bacterium are suspended in nutrient broth. It may be possible to dust lyophilized bacteria onto the plant as a powder, preferably with a powdered carrier as diluent and/or nutrient medium. Noticeable reduction in frost damage is achieved when the bacterium is applied in amounts of one-tenth the concentration described above while application can be made in concentrations greater than that described above although little, if any, additional benefit is derived by more than a ten-fold increase in such concentration.

The exact mechanism of the protection derived from the bacterium M232A has not yet been established. The bacterium M232A may be acting as a competitor which prevents the establishment of the nucleating bacteria and/or the bacterium could be functioning as an inhibitor or antibiotic which destroys the nucleating bacteria or prevents them from growing and/or interferes with their ability to initiate ice formation. Whatever the mechanism, the application of M232A bacterium has been found to be effective to lower the freezing temperature and protect the plant against ice formation or frost damage or freezing in the presence of ice nucleation active bacteria.

Thus the control against frost damage appears to be biological rather than physical or physiochemical, as with water, smudge or wind machines.

The following example (See FIG. 1) will illustrate the effectiveness of M232A in preventing freezing damage, under controlled conditions, in a growth room.

Four days before exposure to freezing temperature, and at intervals thereafter, groups of 3-leaf stage corn plants were sprayed with $7 \times 10^8$ cells/ml of M232A bacterium in a nutrient broth. Separate treatment of another group of the same plants was made with the same nutrient broth, but without M232A, as a control.

Similar treatments were made at intervals up to one day before freezing. At two days before freezing, all plants in all treatments, with and without M232A, were sprayed with $5.5 \times 10^5$ cells/ml of ice nucleation active E. herbicola isolate No. 26 in 0.1 M $PO_4$ buffer solution at a pH of 7.0.

The plants were all left in a moist chamber, after treatment, until one day before exposure to freezing temperatures as low as about $-6°$ C. The results are set forth in the graph of FIG. 1.

When counts were made on the number of injured leaves/plant of the exposure to freezing conditions, using a grading of 0 to 3 leaves/plant and expressing data as the fraction of leaves which were injured, with 0 indicating no injury, it will be seen from data charted in FIG. 1 that damage was severe (upper curve) when nutrient broth alone (without M232A) was applied.

Treatment of plants with M232A bacterium before the isolate No. 26 was applied (points A-B-C-C), protected the plants against frost damage. Even when ice nucleation active bacteria isolate No. 26 was applied simultaneously with the M232A 2 days before freezing (point E), full protection was obtained. Application of M232A to plants 6 and 12 hours after application of the nucleating bacteria and 42 to 36 hours before freezing respectively (points F and G) also reduced frost damage.

Protection against frost damage was not exhibited when the bacterium M232A was applied to plants 18 and 24 hours (points H and I) after the nucleating bacteria has been applied and 30 to 24 hours before freezing respectively.

The foregoing provides ample evidence that M232A functions to prevent or inhibit damage to plants resulting from exposing them to freezing temperatures even in the presence of an ice nucleation active bacterium. It would appear from the results obtained, however, that M232A bacteria must be applied to the plants at a time prior to freezing which will permit them adequate establishment on the plant to compete with, destroy or inhibit the growth of ice nucleation active organisms.

Thus, the present invention provides a relatively simple biological means for reducing frost damage resulting from the exposure of crops and plants to freezing temperatures down to about $-6°$ C. Moreover, the freezing damage control is provided without apparent interference of the normal growth of the plants or crops and without in any way introducing pollutants which might otherwise be objectionable.

It will be understood that other isolates similar in effect to the M232A bacterium may be used for plant protection and that changes may be made in the details of formulation, application and operation without departing from the spirit of the invention, especialy as defined in the following claims.

We claim:

1. The protection of plants against frost damage comprising treating the plants with a bacterium identified as M232A (*Erwinia herbicola* var. anamus) at a time prior to onset of freezing temperature sufficient to permit adequate propagation for establishment and distribution of the bacterium over the plants.

2. The protection as claimed in claim 1 in which the bacterium is non-phytotoxic.

3. The protection of plants as claimed in claim 1 in which the bacterium is applied to the plants with nutrient media.

4. The protection of plants as claimed in claim 1 in which treatment is effected by spraying the plants with a liquid medium containing the bacterium in suspension.

* * * * *